United States Patent
Erkens et al.

(10) Patent No.: US 10,406,080 B2
(45) Date of Patent: Sep. 10, 2019

(54) DOUBLE CHAMBER POUCH FOR THE BLEACHING OF HUMAN HAIR

(71) Applicant: Henkel AG & Co. KGaA, Duesseldorf (DE)

(72) Inventors: Udo Erkens, Willich (DE); Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/728,505

(22) Filed: Oct. 10, 2017

(65) Prior Publication Data

US 2018/0098920 A1  Apr. 12, 2018

(30) Foreign Application Priority Data

Oct. 12, 2016  (DE) .................. 10 2016 219 868

(51) Int. Cl.
| | | |
|---|---|---|
| *A61K 8/02* | (2006.01) | |
| *A61K 8/19* | (2006.01) | |
| *A61K 8/23* | (2006.01) | |
| *A61K 8/25* | (2006.01) | |
| *A61Q 5/08* | (2006.01) | |
| *A61K 8/81* | (2006.01) | |

(52) U.S. Cl.
CPC ............... *A61K 8/022* (2013.01); *A61K 8/19* (2013.01); *A61K 8/23* (2013.01); *A61K 8/25* (2013.01); *A61K 8/8147* (2013.01); *A61Q 5/08* (2013.01); *A61K 2800/88* (2013.01); *A61K 2800/882* (2013.01)

(58) Field of Classification Search
None
See application file for complete search history.

(56) References Cited

U.S. PATENT DOCUMENTS

| | | | | |
|---|---|---|---|---|
| 5,116,388 A | * | 5/1992 | Brooks ................... | A61K 8/02 252/186.25 |
| 2015/0174019 A1 | | 6/2015 | Kleen et al. | |
| 2015/0238391 A1 | * | 8/2015 | Schoepgens ............ | A61K 8/25 424/62 |
| 2016/0102278 A1 | * | 4/2016 | Labeque ............... | C11D 17/042 510/296 |
| 2017/0290749 A1 | | 10/2017 | Borgnini et al. | |
| 2018/0098925 A1 | | 4/2018 | Erkens et al. | |

FOREIGN PATENT DOCUMENTS

| | | |
|---|---|---|
| DE | 4436863 C1 | 1/1996 |
| FR | 2999910 A1 | 6/2014 |
| WO | 9416672 A1 | 8/1994 |
| WO | 03089330 A1 | 10/2003 |
| WO | 2014029657 A2 | 2/2014 |
| WO | 2016074854 A1 | 5/2016 |

OTHER PUBLICATIONS

Intellectual Property Office, Search Report under Section 17(5) for United Kingdom Patent Application No. GB1716540.8 dated Jun. 21, 2018.

* cited by examiner

*Primary Examiner* — Jessica Worsham
(74) *Attorney, Agent, or Firm* — Lorenz & Kopf, LLP

(57) ABSTRACT

The present disclosure relates to a cosmetic agent for lightening keratin fibers, which contains two separate powder-formed preparations (A) and (B), each of which is packaged in a water-soluble film, and a method for lightening keratin fibers using the agent. The cosmetic agent of the present disclosure does not require the use of free hydrogen peroxide.

20 Claims, No Drawings

DOUBLE CHAMBER POUCH FOR THE BLEACHING OF HUMAN HAIR

CROSS-REFERENCE TO RELATED APPLICATION

This application claims priority to German Patent Application No. 10 2016 219 868.8, filed Oct. 12, 2016, which is incorporated herein by reference in its entirety.

TECHNICAL FIELD

The present disclosure relates to a cosmetic agent for lightening keratin fibers, which contains two separate solid preparations (A) and (B), each of which is packaged in a water-soluble film, and a method for lightening keratin fibers using the composition.

BACKGROUND

The oxidizing agents contained in bleaching agents are able to lighten the hair fibers by the oxidative destruction of the hair's dye melanin. For a moderate bleaching effect, the use of hydrogen peroxide, if necessary using ammonia or other alkalizing agents, is sufficient as oxidizing agent alone; for the achievement of a stronger bleaching effect, a mixture of hydrogen peroxide and peroxodisulfate salts and/or peroxomonosulfate salts is usually used.

However, aqueous hydrogen peroxide solutions are unstable at the alkaline Ph values required for the application, so that commercially available oxidative dyeing and bleaching products generally consist of at least two components. The first component is an acid-adjusted oxidizing agent preparation with hydrogen peroxide, which is mixed with an alkaline-adjusted second component shortly before use. For reasons of stability, commercially available bleaching agents are therefore usually offered in two preparations which are packaged separately from one another, which are mixed into a ready-to-use application immediately before use. Usually, commercially available bleaching agents consist of a liquid oxidizing agent preparation and a powder which contains solid oxidizing agents. Since these powders are often offered in doses, however, there is the danger of overdosing.

WO 03/089330 A1 discloses a permanent hair dyeing composition in which the dyeing ingredients, developers and oxidizing agents are contained in a flexible two-chamber container which allows the two dyeing components to be pressed out with the fingers. DE 4436863 C1 describes a two-chamber container for hair coloring agents, which allows dosing of the dyeing components by employing a mechanical closure system. The containers described in these printed documents have the disadvantage in that there is then a remaining container which has to be disposed of. Furthermore, the use of hydrogen peroxide as an oxidizing agent is described in both printed documents, which can lead to irritation, or even triggering allergies in extreme cases, with improper handling of a liquid component, for example by contact with skin parts or eyes.

WO 2016/074854 A1 discloses a cosmetic agent for whitening keratin fibers in which one of the components is packaged in a water-soluble film and the other component is again an aqueous oxidizing agent solution.

BRIEF SUMMARY

In an exemplary embodiment, a cosmetic agent for lightening keratin fibers includes at least two preparations (A) and (B) packaged separately from one another. Preparation (A), based on its total weight, comprises: (a) magnesium carbonate in an amount of from about 5 to about 30% by weight; (b) hydrated sodium silicate having a molar ratio $Na_2O:SiO_2$ of from about 1:2 to about 1:3 in an amount of from about 25 to about 50% by weight; (c) potassium peroxodisulfate in an amount of from about 20 to about 50% by weight; and (d) anunoniwn peroxodisulfate in an amount of from about 1 to about 20% by weight. Preparation (B), based on its total weight, comprises at least one member from the group consisting of percarbamide, percarbonates, and perborates in a total quantity of from 0.5 to 95% by weight. The preparations (A) and (B) are packaged in a water-soluble film.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure is to provide a bleaching agent in which there is no danger of overdosing, which results in less waste to be disposed of and in which a liquid hydrogen peroxide solution is no longer required. The bleaching agent should thereby have excellent blonding properties.

Surprisingly, it has now been found that this can be achieved by a cosmetic agent for whitening keratin fibers in which both components are present in powder form or in solid form, wherein both components are present packaged separated from one another in a water-soluble film and the two components contain defined ingredients.

The present disclosure relates to:
1. A cosmetic agent for whitening keratin fibers, containing at least two preparations (A) and (B) packaged separately from one another, wherein the preparation (A), based on its total weight, contains
   (a) magnesium carbonate in an amount of from about 5 to about 30% by weight,
   (b) hydrated sodium silicate having a molar ratio $Na_2O:SiO_2$ of from about 1:2 to about 1:3 in an amount of from about 25 to about 50% by weight,
   (c) potassium peroxodisulfate in an amount of from about 20 to about 50% by weight and
   (d) ammonium peroxodisulfate in an amount of from about 1 to about 20% by weight,
the preparation (B), based on its total weight, contains at least one member from the group consisting of percarbamide, percarbonates and perborates in a total quantity of from about 0.5 to about 95% by weight, and
the preparations (A) and (B) are packaged in a water-soluble film.
2. Agent according to point 1, wherein the agent is assembled as a two-chambered pouch that contains the preparations (A) and (B) in the two chambers.
3. Agent according to point 1 or 2, wherein the preparation (A) further comprises (e) sodium peroxodisulfate in an amount of from about 1 to about 15% by weight, such as from about 1 to about 10% by weight.
4. Agent according to one of the preceding points, wherein the preparation (B) further contains a filler, such as magnesium carbonate.
5. Agent according to any one of the preceding points, wherein the preparation (A), based on its total weight, contains
the magnesium carbonate (a) in an amount of from about 10 to about 20% by weight,
the hydrated sodium silicate (b) having a molar ratio $Na_2O:SiO_2$ of from about 1:2 to about 1:3 in an amount of from about 35 to about 45% by weight,
the potassium peroxodisulfate (c) in an amount of from about 25 to about 35% by weight and
the ammonium peroxodisulfate (d) in an amount of from about 5 to about 15% by weight.

6. Agent according to any one of the preceding points wherein the hydrated sodium silicate (b) has a molar ratio of $Na_2O: SiO_2$ of from about 1:2.5 to about 1:2.8.

7. Agent according to one of the preceding points, wherein the preparation (B) contains the percarbamide, percarbonate and/or perborate in a total quantity of from about 35 to about 95% by weight, based on their total weight.

8. Agent according to one of the preceding points, wherein the water-soluble film, based on its total weight, consists of at least 60% by weight of a polymer mixture which has a multi-modal molecular weight distribution.

9. Agent according to point 8, wherein the polymer mixture comprises, based on its total weight, at least 60% by weight, such as at least 80% by weight, particularly at least 90% by weight, for example at least 95% by weight, of a mixture comprising
a1) water-soluble vinyl alcohol/vinyl acetate copolymer a1) and
a2) at least one water-soluble vinyl alcohol/vinyl acetate copolymers a2) other than he water-soluble vinyl alcohol/vinyl acetate copolymer a1), or
a mixture, comprising
a1) water-soluble vinyl alcohol/vinyl acetate copolymer a1) and
a2) at least one optionally modified water-soluble polysaccharide, for example at least one water-soluble polysaccharide from the group of methylcellulose, carboxymethylcellulose, ethylcellulose, hydroxyethylcellulose, hydroxypropylcellulose, hydroxypropylmethylcellulose, dextrin and hydroxypropylstarch, such as at least one water-soluble polysaccharide from the group of hydroxypropyl starches.

10. Agent according to one of the preceding points, in which the preparations (A) and (B) are present as powders.

11. Agent according to one of the preceding points, in which the preparation (B) contains only percarbamide as an peroxidant.

12. Agent according to any one of the preceding claims, wherein the preparation (A) and the preparation (B) contain no free hydrogen peroxide.

13. Agent according to one of the preceding claims, wherein the weight ratio of preparation (A) to preparation (B) is from about 10:1 to about 1:10, such as from about 5:1 to about 1:5, for example from about 3:1 to about 1:3.

14. Method for whitening keratin fibers using the cosmetic agent according to one of the preceding points, in which an application mixture is prepared from at least two separate preparations (A) and (B) packaged separately from one another, in which the preparations (A) and (B) packaged in a water-soluble film are added to water in order to dissolve the water-soluble films, wherein the volume ratio of the totality of the preparations (A) and (B) to the water is from about 1:1 to about 1:5, such as from about 1:2 to about 1:3, and subsequently keratin fibers are treated with the application mixture.

15. Method according to point 14, wherein the preparations (A) and (B) are packaged together in a two-chambered pouch and are put into the water to prepare the application mixture of the two-chambered pouches.

The magnesium carbonate and the hydrated, water-soluble magnesium silicate contained in the specified amounts and the peroxodisulfates could surprisingly ensure in combination with the oxidizing agent contained in preparation (B), that after dissolution of the water-soluble film and mixing of the preparations (A) and (B), an effective bleaching application mixture results without the need for hydrogen peroxide.

In principle, all animal hair, e.g. wool, horse hair, angora hair, furs, feathers and products or textiles made from them can be used as keratin-containing fibers. However, exemplary embodiments herein are used for the treatment of human hair and wigs produced therefrom.

An essential constituent of the preparation (A) of the agent as contemplated herein is magnesium carbonate (a). More specifically, this is the commercially available magnesium hydroxide carbonate (usual structural formula $4MgCO_3 \cdot Mg(OH)_2 \cdot 4-5H_2O$. The preparation (A) contains the magnesium carbonate in an amount of from about 5.0 to about 30% by weight, such as from about 10 to about 20% by weight, based on the total weight of the preparation (A).

Furthermore, the preparation (A) contains hydrated sodium silicate as an essential component (b). This is a water-soluble sodium silicate with a molar ratio of $Na_2O:SiO_2$ of from about 1:2 to about 1:3, such as from about 1:2.5 to about 1:2.8. A hydrated sodium silicate particularly suitable as contemplated herein is commercially available under the designation Britesil® 265 (PQ Corporation). The hydrated sodium silicate acts as an alkalizing agent. The preparation (A) contains the hydrated sodium silicate in an amount of from about 25 to about 50% by weight, such as from about 30 to about 45% by weight, for example from about 35 to about 45% by weight, based on the total weight of the preparation (A).

In certain embodiments, the preparation (A) may contain further alkalizing agents, but in certain embodiments no further alkalizing agents are present. In further embodiments, in addition to the sodium metasilicate (b), water-free sodium metasilicate is also present in small amounts.

Moreover, the preparation (A) contains potassium peroxodisulfate (c) as a bleaching agent in a proportion of from about 20 to about 50% by weight and ammonium peroxodisulfate (d) in a proportion of from about 1 to about 20% by weight, based in each case on the total weight of the preparation (A). The preparation (A) contains the potassium peroxodisulfate (c) such as in an amount of 20 to 40% by weight, for example from about 25 to about 35% by weight. The preparation (A) contains the ammonium peroxodisulfate (d) such as in an amount of from about 2 to about 15% by weight, for example from about 5 to about 15% by weight. The preparation (A) can also contain sodium peroxodisulfate (e) in an amount of from about 1 to about 15% by weight, such as from about 1 to about 10% by weight.

In an exemplary embodiment, the total amount of the bleaching agent contained in the preparation (A) is from about 30 to about 60% by weight, such as from about 35 to about 55% by weight, based on the total weight of the preparation (A).

In an exemplary embodiment, the preparation (B) contains percarbamide (addition compound of hydrogen peroxide and urea), percarbonate ($2 Na_2CO_3 \cdot 3H_2O_2$) and/or perborate (sodium perborate) as a further oxidizing agent to the oxidizing agent of the preparation (A) in a total amount of from about 0.5 to about 95% by weight, such as from about 30 to about 60% by weight, for example from about 35 to about 55% by weight, such as from about 40 to about 50% by weight, based on their total weight. In an exemplary embodiment, only percarbamide is used as the oxidizing agent of preparation (B).

In certain embodiments, as a further constituent, the preparation (B) contains a filler, such as a powdered filler. As contemplated herein, magnesium carbonate is an exemplary filler. In certain embodiments, the preparation (B) contains no further components apart from the oxidizing agent and the filler.

A higher viscosity of the composition may be advantageous in order to be able to apply the application mixture from preparation (A) and (B) cleanly and locally. For this purpose, it is advantageous if the composition is not a paste, a viscous cream or a concentrated gel but rather has a sufficient flowability. Furthermore, the ready-to-use agent must have rheological properties which allow application to the fibers to be bleached but at the same time prevent the agent from running or flowing out from the site of action during the period of use. Exemplary application mixtures have a viscosity of from about 5 to about 100 Pa·s, such as from about 10 to about 50 Pa·s, for example from about 10 to about 20 Pa·s, such as from about 10 to about 16 Pa·s (Brookfield, 22° C., spindle #5, 4 rpm). Exemplary preparations (A) or (B), such as only (A), contain at least one thickening agent and/or at least one gelling agent. Inorganic as well as organic substances are suitable as thickening agents or gelling agents.

The thickening agent can be selected, for example, from the polymeric thickening agents known under the following INCI designations: acrylamide copolymer, acrylamide/sodium acrylate copolymer, acrylamide/sodium acryloyldimethyltaurate copolymer, acrylates/acetoacetoxyethyl methacrylate copolymer, acrylates/beheneth-25 methacrylate copolymer, acrylates/C 10-30 alkyl acrylate cross-polymer, acrylate/ceteth-20 itaconate copolymer, acrylates/ceteth-20 methacrylate copolymer, acrylates/laureth-25 methacrylate copolymer, acrylate/palmeth-25 acrylate copolymer, acrylate/palmeth-25 itaconate copolymer, acrylate/steareth-50 acrylate copolymer, acrylate/steareth-20 itaconate copolymer, acrylates/steareth-20 methacrylate copolymer, acrylate/stearyl methacrylate copolymer, acrylate/vinyl isodecanoate cross-polymer, acrylic acid/acrylonitrogen copolymer, agar, agarose, alcaligenes polysaccharides, algin, alginic acid, ammonium acrylates/acrylonitrogenic copolymer, ammonium acrylate copolymer, ammonium acryloyldimethyltaurate/vinylformamide copolymer, ammonium acryloyldimethyltaurates/VP copolymer, ammonium alginates, ammonium polyacryloyldimethyl taurates, amylopectin, ascorbyl methylsilanol pectinates, astragalus gummifer gum, attapulgite, avena sativa (oat) kernel flour, bentonite, butoxy chitosan, caesalpinia spinosa gum, calcium alginates, calcium carboxymethyl cellulose, calcium carrageenan, calcium potassium carbomer, calcium starch octenylsuccinate, C20-40 alkyl stearate, carbomer, carboxymethyl chitosan, carboxymethyl chitin, carboxymethyl chitosan, carboxymethyl dextran, carboxymethyl hydroxyethyl cellulose, carboxymethyl hydroxypropyl guar, cellulose acetates propionates carboxylates, cellulose gum, ceratonia siliqua gum, cetyl hydroxyethylcellulose, cholesterol/HDI/pullulan copolymer, cholesteryl hexyl dicarbamate pullulan, cyamopsis tetragonoloba (guar) gum, diglycol/CHDM/isophthalates/sip copolymer, dihydrogenated tallow benzylmonium hectorite, dimethicone crosspolymer-2, dimethicone propyl pg betaines, DMAPA acrylates/acrylic acid/acrylonitrogen copolymer, ethylene/sodium acrylate copolymer, gelatin, gellan gum, glyceryl alginates, glycine soybean (soybean) flour, guar hydroxypropyltrimonium chloride, hectorite, hydrated silica, hydrogenated potato starch, hydroxybutyl methylcellulose, hydroxyethyl acrylate/sodium acryloyldimethyl taurate copolymer, hydroxyethylcellulose, hydroxyethyl chitosan, hydroxyethyl ethyl cellulose, hydroxypropyl cellulose, hydroxypropyl chitosan, hydroxypropyl ethylene diamines carbomer, hydroxypropyl guar, hydroxypropyl methylcellulose, hydroxypropylmethylcellulose stearyl ether, hydroxystearamides MEA, isobutylene/sodium maleate copolymer, lithium magnesium silicate, lithium magnesium sodium silicate, macrocystis pyrifera (kelp), magnesium alginate, magnesium aluminum silicates, magnesium silicates, magnesium trisilicates, methoxy PEG-22/dodecyl glycol copolymer, methyl cellulose, methyl ethyl cellulose, methyl hydroxyethylcellulose, microcrystalline cellulose, montmorillonite, moroccan lava clay, natto gum, nonoxynyl hydroxyethylcellulose, octadecenes/MA copolymer, pectin, PEG-800, PEG-crosspolymer, PEG-150/decyl alcohol/SMDI copolymer, PEG-175 diisostearate, PEG-190 distearates, PEG-15 glyceryl tristearates, PEG-140 glyceryl tristearates, PEG-240/HDI copolymer bis-decyltetradeceth-20 ether, PEG-100/IPDI copolymer, PEG-180/laureth-50/TMMG copolymer, PEG-10/lauryl dimethicone crosspolymer, PEG-15/lauryl dimethicone crosspolymer, PEG-2M, PEG-5M, PEG-7M, PEG-9M, PEG-14M, PEG-20M, PEG-23M, PEG-25M, PEG-45M, PEG-65M, PEG-90M, PEG-1 15M, PEG-160M, PEG-120 methyl glucose trioleate, PEG-180/octoxynol-40/TMMG copolymer, PEG-150 pentaerythrityl tetrastearate, PEG-4 rapeseedamide, PEG-150/stearyl alcohol/SMDI copolymer, polyacrylate-3, polyacrylic acid, polycyclopentadienes, polyether-1, polyethylenes/isopropyl maleates/MA copolyol, polymethacrylic acid, polyquaternium 52, polyvinyl alcohol, potassium alginates, potassium aluminum polyacrylates, potassium carbomer, potassium carrageenan, potassium polyacrylate, potato starch modified, PPG-14 laureth-60 hexyl dicarbamate, PPG-14 laureth-60 isophoryl dicarbamate, PPG-14 palmeth-60 hexyl dicarbamate, propylene glycol alginate, PVP/decene copolymer, PVP montmorillonite, rhizobian gum, ricinoleic acid/adipic acid/AEEA copolymer, sclerotium gum, sodium acrylate/acryloyldimethyl taurate copolymer, sodium acrylate/acrolein copolymer, sodium acrylate/acrylonitrogen copolymer, sodium acrylate copolymer, sodium acrylates/vinyl isodecanoate crosspolymer, sodium acrylate/vinyl alcohol copolymer, sodium carboxymethyl chitin, sodium carboxymethyl dextran, sodium carboxymethyl beta-glucan, sodium carboxymethyl starch, sodium carrageenan, sodium cellulose sulfates, sodium cyclodextrin sulfates, sodium hydroxypropyl starch phosphates, sodium isooctylene/MA copolymer, sodium magnesium fluorosilicates, sodium polyacrylates, sodium polyacrylates starch, sodium polyacryloyldimethyl taurates, sodium polymethacrylates, sodium polystyrene sulfonates, sodium silicoaluminates, sodium starch octenylsuccinate, sodium stearoxy PG-hydroxyethylcellulose sulfonates, sodium styrene/acrylates copolymer, sodium tauride acrylate/acrylic acid/acrylonitrogen copolymer, solanum tuberosum (potato) starch, starch/acrylates/acrylamide copolymer, starch hydroxypropyltrimonium chloride, steareth-60 cetyl ether, steareth-100/PEG-136/HDI copolymer, sterculia urens gum, synthetic fluorphlogopite, tamarindus indica seed gum, tapioca starch, TEA alginate, TEA carbomer, triticum vulgare (wheat) starch, tromethamine acrylates/acrylonitrogen copolymer, tromethamine magnesium aluminum silicate, welan gum, yeast beta glucan, yeast polysaccharides, zea mays (corn) starch.

In an exemplary embodiment, the thickening agent or gelling agent is selected from polyacrylic acid, carboxymethyl cellulose, silica, a copolymer of methacrylic acid and methyl methacrylate, and a combination thereof.

In certain embodiments, the combination of carboxymethylcellulose (for example Cekol® 50000 ex CP Kelco (INCI: cellulose gum)), a methacrylic acid/methylmethacrylate copolymer (for example Rohagit® S hv ex Evonik (INCI: acrylate copolymer) and silicic acid as a constituent of the preparation (A), while the preparation (B) contains a combination of polyacrylic acid and silicic acid.

In certain embodiments, the polymeric thickening agents and gelling agents are present in a total amount of from about 0.5 to about 20% by weight, such as from about 1.0 to about 10% by weight, in the preparation (A).

In certain embodiments, the polymeric thickening agents and gelling agents are present in the total amount of from about 0.1 to about 10% by weight, such as from about 0.4 to about 5.0% by weight, in the preparation (B).

The selection of the amount and chemical nature of the thickening agents and gelling agents not only influences the viscosity of the application mixture from preparation (A) and (B) but also the dissolution properties of the preparations (A) and (B). The exemplary thickening agents/gelling agents listed above also may have a particularly advantageous effect on the dissolution properties of the preparations (A) and (B).

The composition of some cosmetic preparations as contemplated herein can be found in the following tables (in % by weight, based on the total weight of preparations (A) and (B), unless otherwise specified.

|  | Formula 1 | Formula 2 | Formula 3 | Formula 4 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| other ingredients | ad 100 | ad 100 | ad 100 | ad 100 |
| Preparation (B) | | | | |
| Percarbamide, percarbonate and/or perborate | 0.5 to 95 | 30 to 60 | 35 to 55 | 40 to 50 |
| other ingredients | ad 100 | ad 100 | ad 100 | ad 100 |

|  | Formula 6 | Formula 7 | Formula 8 | Formula 9 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| other ingredients | ad 100 | ad 100 | ad 100 | ad 100 |
| Preparation (B) | | | | |
| Percarbamide | 0.5 to 95 | 30 to 60 | 35 to 55 | 40 to 50 |
| other ingredients | ad 100 | ad 100 | ad 100 | ad 100 |

|  | Formula 11 | Formula 12 | Formula 13 | Formula 14 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| Thickening and/or gelling agent | 0.5 to 20 | 0.5 to 15 | 1.0 to 12 | 1.0 to 10 |
| other ingredients | ad 100 | ad 100 | ad 100 | ad 100 |
| Preparation (B) | | | | |
| Percarbamide, percarbonate and/or perborate | 0.5 to 95 | 30 to 60 | 35 to 55 | 40 to 50 |
| other ingredients | ad 100 | ad 100 | ad 100 | ad 100 |

|  | Formula 16 | Formula 17 | Formula 18 | Formula 19 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| Thickening and/or gelling agent | 0.5 to 20 | 0.5 to 15 | 1.0 to 12 | 1.0 to 10 |
| other ingredients | ad 100 | ad 100 | ad 100 | ad 100 |
| Preparation (B) | | | | |
| Percarbamide | 0.5 to 95 | 30 to 60 | 35 to 55 | 40 to 50 |
| other ingredients | ad 100 | ad 100 | ad 100 | ad 100 |

-continued

|  | Formula 21 | Formula 22 | Formula 23 | Formula 24 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| other ingredients | ad 100 | ad 100 | ad 100 | ad 100 |
| Preparation (B) | | | | |
| Percarbamide, percarbonate and/or perborate | 0.5 to 95 | 30 to 60 | 35 to 55 | 40 to 50 |
| Thickening and/or gelling agent | 0.1 to 10 | 0.2 to 8.0 | 0.3 to 6.0 | 0.4 to 5.0 |
| other ingredients | ad 100 | ad 100 | ad 100 | ad 100 |

|  | Formula 26 | Formula 27 | Formula 28 | Formula 29 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| other ingredients | ad 100 | ad 100 | ad 100 | ad 100 |
| Preparation (B) | | | | |
| Percarbamide | 0.5 to 95 | 30 to 60 | 35 to 55 | 40 to 50 |
| Thickening and/or gelling agent | 0.1 to 10 | 0.2 to 8.0 | 0.3 to 6.0 | 0.4 to 5.0 |
| other ingredients | ad 100 | ad 100 | ad 100 | ad 100 |

|  | Formula 31 | Formula 32 | Formula 33 | Formula 34 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| Thickening and/or gelling agent | 0.5 to 20 | 0.5 to 15 | 1.0 to 12 | 1.0 to 10 |
| other ingredients | ad 100 | ad 100 | ad 100 | ad 100 |
| Preparation (B) | | | | |
| Percarbamide, percarbonate and/or perborate | 0.5 to 95 | 30 to 60 | 35 to 55 | 40 to 50 |
| Thickening and/or gelling agent | 0.1 to 10 | 0.2 to 8.0 | 0.3 to 6.0 | 0.4 to 5.0 |
| other ingredients | ad 100 | ad 100 | ad 100 | ad 100 |

|  | Formula 36 | Formula 37 | Formula 38 | Formula 39 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| Thickening and/or gelling agent | 0.5 to 20 | 0.5 to 15 | 1.0 to 12 | 1.0 to 10 |
| other ingredients | ad 100 | ad 100 | ad 100 | ad 100 |
| Preparation (B) | | | | |
| Percarbamide | 0.5 to 95 | 30 to 60 | 35 to 55 | 40 to 50 |
| Thickening and/or gelling agent | 0.1 to 10 | 0.2 to 8.0 | 0.3 to 6.0 | 0.4 to 5.0 |
| other ingredients | ad 100 | ad 100 | ad 100 | ad 100 |

|  | Formula 41 | Formula 42 | Formula 43 | Formula 44 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |

-continued

| | | | | |
|---|---|---|---|---|
| Methacrylic acid/methyl methacrylate copolymer, carboxymethylcellulose and/or silicic acid | 0.5 to 20 | 0.5 to 15 | 1.0 to 12 | 1.0 to 10 |
| other ingredients | ad 100 | ad 100 | ad 100 | ad 100 |
| Preparation (B) | | | | |
| Percarbamide, percarbonate and/or perborate | 0.5 to 95 | 30 to 60 | 35 to 55 | 40 to 50 |
| other ingredients | ad 100 | ad 100 | ad 100 | ad 100 |

| | Formula 46 | Formula 47 | Formula 48 | Formula 49 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| Methacrylic acid/methyl methacrylate copolymer, carboxymethylcellulose and/or silicic acid | 0.5 to 20 | 0.5 to 15 | 1.0 to 12 | 1.0 to 10 |
| other ingredients | ad 100 | ad 100 | ad 100 | ad 100 |
| Preparation (B) | | | | |
| Percarbamide | 0.5 to 95 | 30 to 60 | 35 to 55 | 40 to 50 |
| other ingredients | ad 100 | ad 100 | ad 100 | ad 100 |

| | Formula 51 | Formula 52 | Formula 53 | Formula 54 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| other ingredients | ad 100 | ad 100 | ad 100 | ad 100 |
| Preparation (B) | | | | |
| Percarbamide, percarbonate and/or perborate | 0.5 to 95 | 30 to 60 | 35 to 55 | 40 to 50 |
| Polyacrylic acid and/or silicic acid | 0.1 to 10 | 0.2 to 8.0 | 0.3 to 6.0 | 0.4 to 5.0 |
| other ingredients | ad 100 | ad 100 | ad 100 | ad 100 |

| | Formula 56 | Formula 57 | Formula 58 | Formula 59 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| other ingredients | ad 100 | ad 100 | ad 100 | ad 100 |
| Preparation (B) | | | | |
| Percarbamide | 0.5 to 95 | 30 to 60 | 35 to 55 | 40 to 50 |
| Polyacrylic acid and/or silicic acid | 0.1 to 10 | 0.2 to 8.0 | 0.3 to 6.0 | 0.4 to 5.0 |
| other ingredients | ad 100 | ad 100 | ad 100 | ad 100 |

| | Formula 61 | Formula 62 | Formula 63 | Formula 64 |
|---|---|---|---|---|
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| Methacrylic acid/methyl methacrylate copolymer, carboxymethylcellulose and/or silicic acid | 0.5 to 20 | 0.5 to 15 | 1.0 to 12 | 1.0 to 10 |
| other ingredients | ad 100 | ad 100 | ad 100 | ad 100 |
| Preparation (B) | | | | |
| Percarbamide, percarbonate and/or perborate | 0.5 to 95 | 30 to 60 | 35 to 55 | 40 to 50 |

| -continued | | | | |
|---|---|---|---|---|
| Polyacrylic acid and/or silicic acid | 0.1 to 10 | 0.2 to 8.0 | 0.3 to 6.0 | 0.4 to 5.0 |
| other ingredients | ad 100 | ad 100 | ad 100 | ad 100 |
| | Formula 66 | Formula 67 | Formula 68 | Formula 69 |
| Preparation (A) | | | | |
| Magnesium carbonate | 5.0 to 30 | 7.0 to 25 | 7.0 to 25 | 10 to 20 |
| Sodium silicate* | 25 to 50 | 30 to 45 | 35 to 45 | 35 to 45 |
| Potassium peroxodisulfate | 20 to 50 | 20 to 40 | 20 to 40 | 25 to 35 |
| Ammonium peroxodisulfate | 1.0 to 20 | 2.0 to 15 | 2.0 to 15 | 5.0 to 15 |
| Methacrylic acid/methyl methacrylate copolymer, carboxymethylcellulose and/or silicic acid | 0.5 to 20 | 0.5 to 15 | 1.0 to 12 | 1.0 to 10 |
| other ingredients | ad 100 | ad 100 | ad 100 | ad 100 |
| Preparation (B) | | | | |
| Percarbamide | 0.5 to 95 | 30 to 60 | 35 to 55 | 40 to 50 |
| Polyacrylic acid and/or silicic acid | 0.1 to 10 | 0.2 to 8.0 | 0.3 to 6.0 | 0.4 to 5.0 |
| other ingredients | ad 100 | ad 100 | ad 100 | ad 100 |

*hydrated sodium silicate with a molar ratio of $Na_2O:SiO_2$ of from about 1:2 to about 1:3

In certain embodiments, the preparations (A) and (B) are packaged separately in a water-soluble film, such as in a two-chambered pouch, in which both preparations are packaged separately from one another; the chambers however are connected to each other by film or the chambers have film between them as a partition wall. However, the present disclosure also includes embodiments, so-called kits-of-parts, in which the preparations (A) and (B) are each separately packaged in a water-soluble film and the chambers are not connected to each other. In particular in the latter cases, the preparations (A) and (B) can be packaged in the same or different water-soluble films.

Water-soluble films are known per se. With regard to the dissolution speed and also the consistency of the resulting application mixture, the exemplary water-soluble film contains a polymer mixture whose molecular weight distribution is multi-modal. In other words, the density of the frequency distribution of the molecular weight has at least two modes (maxima), for example two, three, four, five or more modes. The exemplary water-soluble film may contain a polymer mixture with a bimodal molecular weight distribution since, as described at the outset, such a mixture may have, on the one hand, a very advantageous effect on the product properties of cosmetic agents as contemplated herein, and on the other hand, a bimodal distribution can be implemented more simply than a tri- or multi-modal frequency distribution.

An exemplary bimodal molecular weight distribution may be symmetric or asymmetric.

In an exemplary multi-modal, such as bimodal, molecular weight distribution, the molecular weights differ by at least two of the modes based on the smallest molecular weight which can be assigned to a mode by from about 5% to about 120%, such as by from about 10% to about 90%, and for example by from about 20% to about 60%

In a further multi-modal, such as bimodal, molecular weight distribution, the frequency of the two-mode minimum differs from the frequency of the least of these two modes (least-frequent mode) by from about 5% to about 80%, such as from about 10% to about 60%, for example from about 20% to about 40%, in each case based on the frequency of the smallest of the two modes. For the application properties of agents as contemplated herein, in particular the fast and residue-free preparation of the hair cosmetic application mixture, it may be advantageous if the water-soluble film, based on its own weight, consists of at least about 70% by weight, such as at least about 80% by weight, for example at least about 90% by weight, such as at least about 95% by weight, of a polymer mixture which has a multi-modal molecular weight distribution. Again, a bimodal molecular weight distribution may be suitable.

Polymer mixtures which have a polydispersity index above 2.2, such as above 3.0, for example above 4.6, have proven to be advantageous for the product properties. The polydispersity index in this case is the ratio of the weight- and number-average molecular weight.

The weight average or the weight-average molecular weight ($M_{mit}$) is defined as $$M_{mit} = \Sigma n_i M_i^2 / n_i M_i$$

with $M_{mit}$=weight-average molecular weight, $n_i$=number of macromolecules in the specimen with exactly i repeating units and $M_i$=molar mass i.

The weighting average is obtained by methods which take into account the size and shape of a molecule in solution, e.g. static light scattering, small-angle X-ray scattering and sedimentation equilibrium measurements.

The number average or the number average molecular weight ($M_n$) is defined as $$M_n = \Sigma n_i M_i^2 / n_i M_i$$

with $M_n$=number-average molar mass, $n_i$=number of macromolecules in the sample with exactly i repeating units and $M_i$=molar mass i.

The number average can be determined by colligative methods, e.g. cryoscopy, membrane or vapor pressure osmometry and, in so far as the number of end groups per molecule is known, by end group determination.

Water-soluble films which do not completely consist of the polymer mixture with the multi-modal molecular weight distribution may contain additional active ingredients or fillers, but also solvents, in particular water, as further ingredients.

The group of the further active ingredients here is, for example, hair-cosmetically active ingredients as well as materials which protect the ingredients of the preparation (A) surrounded by the film material from decomposition or deactivation by light irradiation. Antioxidants, UV absorbers and fluorescent dyes have proven particularly suitable here.

An exemplary water-soluble film may have a water content of from about 3.0 to about 12% by weight, such as from about 4.0 to about 10% by weight, based on its total weight.

The thickness of the water-soluble film(s) used for packaging the preparations (A) and (B) may be from about 0.01 to about 0.1 mm, such as from about 0.01 to about 0.08 mm, for example from about 0.02 to about 0.06 mm.

The water-soluble film into which preparations (A) and (B) are packaged may comprise one or more structurally different water-soluble polymers. Polymers from the group (optionally acetalized) polyvinyl alcohols (PVAL), polyvinylpyrrolidones, polyethylene oxides, gelatin and cellulose are particularly suitable as water-soluble polymer(s).

In a first exemplary embodiment, the polymer mixture having the multi-modal, such as bimodal, molecular weight distribution comprises two vinyl acetate/vinyl alcohol copolymers. Exemplary cosmetic compositions are therefore exemplified in that the polymer mixture comprises, based on its total weight, at least 60% by weight, such as at least about 80% by weight, for example at least about 90% by weight, for example at least about 95% by weight, from a mixture comprising a1) water-soluble vinyl alcohol/vinyl acetate copolymer a1) and a2) at least one water-soluble vinyl alcohol/vinyl acetate copolymer a2) which is different from the water-soluble vinyl alcohol/vinyl acetate copolymer a1).

In the aforementioned embodiment based on two water-soluble vinyl alcohol vinyl acetate copolymers, the polymer mixture has a polydispersity index above about 2.2, such as above about 3.0, for example, above about 4.6, while the polydispersity index of the vinyl alcohol/vinyl acetate copolymer a1) is between about 1.8 and about 2.3.

Particularly advantageous product properties are achieved by vinyl alcohol/vinyl acetate copolymers a1) having a degree of hydrolysis between about 84% and about 90%, such as between about 85% and about 89%, for example between about 86% and about 88%. Corresponding copolymers a1) have, in other words, a residual content of acetyl groups between about 10% and about 16%, such as between about 11% and about 15%, and in particular between about 12% and about 14%.

In addition to the polydispersity index and the degree of hydrolysis, the viscosity of aqueous solutions of the vinyl alcohol/vinyl acetate copolymers has proved to be a exemplary feature of particularly advantageous copolymers. Exemplary cosmetic agents are therefore exemplified in that the vinyl alcohol/vinyl acetate copolymer a1) has a viscosity (20° C., 4% by weight solution in water, measured with a Brookfield LV viscometer with UL adapter) between about 12 cP and about 20 cP, such as between about 14 cP and about 19 cP, for example between about 16 cP and about 18 cP.

On the other hand, the viscosity (20° C., 4% by weight solution in water, measured with a Brookfield LV viscometer with UL adapter) of an exemplary vinyl alcohol/vinyl acetate copolymer a2) is between about 20 cP and about 30 cP, such as between about 20 cP and about 28 cP and in particular between about 20 cP and about 25 cP.

In addition to the above-described combination of two vinyl alcohol/vinyl acetate copolymers, further polymer combinations exist having properties which may be advantageous in view of the aforementioned technical tasks. In an alternative embodiment of the cosmetic agents as contemplated herein, the polymer mixture of the water-soluble film, based on its total weight, consists of at least 60% by weight, such as at least 80% by weight, for example at least 90% by weight, such as at least 95% by weight of a mixture comprising a1) water-soluble vinyl alcohol/vinyl acetate copolymer a1) and a2) at least one optionally modified water-soluble polysaccharide, such as at least one water-soluble polysaccharide from the group of methylcellulose, carboxymethylcellulose, ethylcellulose, hydroxyethylcellulose, hydroxypropylcellulose, hydroxypropylmethylcellulose, dextrin and hydroxypropylstarch, for example at least one water-soluble polysaccharide from the group of hydroxypropyl starches.

The polydispersity index of the aforementioned exemplary polymer mixtures of vinyl alcohol/vinyl acetate copolymers and polysaccharide is in turn above about 2.2, such as above about 3.0 and in particular above about 4.6, while the exemplary vinyl alcohol/vinyl acetate copolymer a1) has a polydispersity index of between about 1.8 and about 2.3.

When the vinyl alcohol/vinyl acetate copolymer a1) is combined with a polysaccharide, the exemplary vinyl alcohol/vinyl acetate copolymer a1) thus has a degree of hydrolysis between about 84% and about 90%, such as between about 85% and about 89% and in particular between 86% and 88%. The viscosity (20° C., 4% by weight solution in water, measured with a Brookfield LV viscosimeter with UL adapter) of the exemplary vinyl alcohol/vinyl acetate copolymer a1) is between about 12 cP and about 20 cP, such as between about 14 cP and 19 CP and in particular between about 16 cP and about 18 cP.

As mentioned above, the viscosity of the application mixture is in selected viscosity ranges. The viscosity of the application mixture obtainable by mixing the preparations (A) and (B) can be adjusted by selecting a suitable polymer mixture for the water-soluble film. The viscosity of the application mixture and its application properties and bleaching effect can thereby be advantageously influenced both by the chemical nature of the polymer mixture and by the amount of the polymer mixture used for the packaging. Exemplary cosmetic agents are therefore exemplified in that the proportion by weight of the polymer mixture having the multi-modal molecular weight distribution of the total weight of the preparations (A) and (B) including the water-soluble film is from about 1 to about 15% by weight, such as from about 2 to about 10% by weight and in particular from about 3 to about 8% by weight.

Further, the preparation (A) and/or (B), such as only (A), can contain further active ingredients, auxiliaries and additives such as, for example, nonionic polymers such as vinylpyrrolidone/vinyl acrylate copolymers, polyvinylpyrrolidone and vinylpyrrolidone/vinyl acetate copolymers and polysiloxanes, cationic polymers such as quaternized cellulose ethers, polysiloxanes having quaternary groups, dimethyldiallylammonium chloride polymers, acrylamide-dimethyldiallylammonium chloride copolymers, with diethylsulfate quaternized dimethylaminoethyl methacrylate-vinylpyrrolidone copolymers, vinylpyrrolidone-imidazolinium-methochloride copolymers, and quaternized polyvinyl alcohol, zwitterionic and amphoteric polymers such as, for example, acrylamidopropyltrimethylammonium chloride/acrylate copolymers and octylacrylamide/methylmethacrylate/tert-butylaminoethylmethacrylate/2-hydroxypropylmethacrylate copolymers, anionic polymers such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methylvinyl ether/maleic acid anhydride copolymers and acrylic acid/ethyl acrylate/ N-tert.-butyl acrylamide terpolymers, solvents and solubilizers such as ethanol, isopropanol, ethylene glycol, propylene glycol, glycerol and diethylene glycol, consistency promoters such as sugar esters, polyol esters or polyol alkyl ethers, stabilizing agents, for example complexing agents such as EDTA, NTA, β-alaninediacetic acid and phosphonic acids.

The preparations (A) and (B) are present in solid form, for example in the form of a powder, a granulate or a compressed body, for example, in the form of a tablet. Exemplary preparations (A) and (B) are in powder form.

The preparations (A) and (B) are water-free as contemplated herein. As contemplated herein, "water-free" means a water content of 1% by weight or less. In an exemplary embodiment, the preparations have a water content of 0.5% by weight or less, more such as 0.2% by weight or less, for example 0.1% by weight or less, such as near 0 or 0% by weight, wherein in each case the content of free, i.e., not bound, water is meant. The free water content can be determined as contemplated herein by the Karl Fischer method.

Exemplary preparations (A) and (B) contain no free hydrogen peroxide and, as contemplated herein, an exemplary cosmetic agent as contemplated herein also contains no additional free hydrogen peroxide.

In exemplary embodiments, weight ratio of the preparation (A) to the preparation (B) in the separate packages is in the range from about 10:1 to about 1:10, such as from about 5:1 to about 1:5 and in particular from about 3:1 to about 1:3, for example about 3:2.

The present disclosure also relates to a method for lightening keratin fibers using the cosmetic agent. In the method as contemplated herein, an application mixture is prepared from at least two separate preparations (A) and (B), which are packaged separately from one another, by adding the preparations (A) and (B) packaged in a water-soluble film into water, in order to dissolve the water-soluble film, and then keratin fibers are treated with the application mixture in the usual manner.

In an exemplary embodiment, the volume ratio of the total of the preparations (A) and (B) to the water is from about 1:1 to about 1:5, such as from about 1:2 to about 1:3.

In certain embodiments, the preparations (A) and (B) are packaged together in a two-chambered pouch, so that the two-chamber pouch is simply put into the water to prepare the application mixture.

As contemplated herein, the application mixture can be applied to the keratin-containing fibers, left on the fibers at a temperature of room temperature to 45° C. for an exposure time of from about 10 to about 60 minutes and then rinsed out with water or washed out with a shampoo.

In an exemplary embodiment, the application time of the ready-for-use lightening agents is 10 to 60 minutes, in particular from about 15 to about 50 minutes, such as from about 20 to about 45 minutes. During the exposure time of the agent to the fiber, it may be advantageous to support the lightening process by supplying heat.

The heat supply can be effected through an external heat source, such as with the aid of a warm air blower, as well as, particularly in the case of hair lightening in the living subject, through the body temperature of the subject. In the case of the latter possibility, the part to be lightened is usually covered with a hood. An exposure phase at room temperature is also as contemplated herein. In an exemplary embodiment, the temperature is between about 20° C. and about 40° C., in particular between about 25° C. and about 38° C., during the exposure time. The lightening agents already give good bleaching and lightening results even at physiologically tolerable temperatures of below 45° C.

After the end of the exposure time, the remaining lightening preparation is rinsed with water or a cleansing agent from the hair. In particular, commercially available shampoo can be used as a cleansing agent, wherein, in particular, the cleaning agent can be dispensed with and the rinsing process can be carried out with tap water if the application mixture contains sufficient surfactants.

The dissolution of the films and the mixing of the two preparations is generally supported by agitation. After thorough stirring or blending, the application mixture is usually applied to the hair with the help of a brush or applicator.

EXAMPLES

The preparations (A) and (B) shown in the following Tables 1 and 2 were prepared. The indications of quantity indicate weight percent.

TABLE 1

| Component | Preparation (A) |
|---|---|
| Ammonium persulfate + 0.5% silica | 10.00 |
| Potassium persulfate | 30.00 |
| Britesil ® C 265 | 39.40 |
| Rohagit ® S hv | 1.00 |
| Cekol ® 50000 | 2.00 |
| Magnesium carbonate, heavy pharm. 400 g/l | 14.70 |
| Silicic acid hydrophilic, BET | 1.00 |
| Celquat ® L-200 | 0.30 |
| EDETA BX Powder | 1.60 |
| Total | 100 |

Ingredients:
Britesil® C 265 (PQ Corporation): water-soluble hydrated sodium silicate with a molar ratio $Na_2O:SiO_2$ of 1:2.65
Rohagit® S hv (Evonik): Copolymer of methacrylic acid and methyl methacrylate
Cekol® 50000 (CP Kelco): Cellulose gum, sodium carboxymethylcellulose
Celquat® L-200 8Akzo Nobel): Polyquaternium-4

TABLE 2

| Component | Preparation (B) |
|---|---|
| Percarbamide | 34.0 |
| Magnesium carbonate | 64.6 |
| Polyacrylic acid | 1.6 |
| Silicic acid hydrophilic, BET | 0.8 |
| Total | 100 |

Preparations (A) and (B) were packed in a two-compartment container of a water-soluble film, wherein the weight ratio of preparation (A) to preparation (B) was 1:1.

The two-chambered pouch was placed in water, which was provided in a volume ratio of about 1 (pouch) to 2 (water). An application mixture was obtained within a few minutes with stirring The application mixture was applied to human hair and exhibited good properties such as distributability, consistency after mixing, feeling on the scalp, and in particular a very good whitening result.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic agent for lightening keratin fibers, the cosmetic agent comprising:
   at least two preparations (A) and (B) packaged separately from one another, wherein the preparation (A), based on its total weight, comprises:
      (a) magnesium carbonate in an amount of from about 5 to about 30% by weight;
      (b) hydrated sodium silicate having a molar ratio $Na_2O$:$SiO_2$ of from about 1:2 to about 1:3 in an amount of from about 25 to about 50% by weight;
      (c) potassium peroxodisulfate in an amount of from about 20 to about 50% by weight; and
      (d) ammonium peroxodisulfate in an amount of from about 1 to about 20% by weight;
   wherein the preparation (B), based on its total weight, comprises at least one member selected from the group consisting of percarbamide, percarbonates, and perborates in a total quantity of from 0.5 to 95% by weight, and wherein the preparations (A) and (B) are packaged in a water-soluble film, wherein the preparation (A) and the preparation (B) are each independently in a powder form and/or in a solid form, and wherein the preparation (A) and the preparation (B) are each independently water-free and contain no free hydrogen peroxide.

2. The cosmetic agent of claim 1, wherein the cosmetic agent is assembled as a two-chambered pouch including a first chamber and a second chamber, and wherein the preparation (A) is in the first chamber and the preparation (B) is in the second chamber.

3. The cosmetic agent of claim 1, wherein the preparation (A) further comprises (e) sodium peroxodisulfate in an amount of from about 1 to about 15% by weight.

4. The cosmetic agent of claim 1, wherein the preparation (A) further comprises (e) sodium peroxodisulfate in an amount of from about 1 to about 10% by weight.

5. The cosmetic agent of claim 1, wherein preparation (B) further comprises a filler.

6. The cosmetic agent of claim 1, wherein preparation (B) further comprises magnesium carbonate as a filler.

7. The cosmetic agent of claim 1, wherein the preparation (A), based on its total weight, comprises:
   the magnesium carbonate (a) in an amount of from about 10 to about 20% by weight;
   the hydrated sodium silicate (b) having a molar ratio $Na_2O$:$SiO_2$ of from about 1:2 to about 1:3 in an amount of from about 35 to about 45% by weight;
   the potassium peroxodisulfate (c) in an amount of from about 25 to about 35% by weight; and
   the ammonium peroxodisulfate (d) in an amount of from about 5 to about 15% by weight.

8. The cosmetic agent of claim 1, wherein the preparation (B) comprises the at least one member selected from the group consisting of percarbamide, percarbonates and perborates in a total amount of from about 35 to about 55% by weight, based on the total weight thereof.

9. The cosmetic agent of claim 1, wherein the water-soluble film, based on its total weight, comprises at least 60% by weight of a polymer mixture having a multi-modal molecular weight distribution.

10. The cosmetic agent of claim 9, wherein the polymer mixture comprises, based on its total weight, at least 60% by weight of:
    a mixture comprising:
       a1) water-soluble vinyl alcohol/vinyl acetate copolymer; and
       a2) at least one water-soluble vinyl alcohol/vinyl acetate copolymers other than the water-soluble vinyl alcohol/vinyl acetate copolymer a1), or
    a mixture, comprising
       a1) water-soluble vinyl alcohol/vinyl acetate copolymer; and
       a2) at least one water-soluble polysaccharide.

11. The cosmetic agent of claim 10, wherein the at least one water-soluble polysaccharide is selected from methylcellulose, carboxymethylcellulose, ethylcellulose, hydroxyethylcellulose, hydroxypropylcellulose, hydroxypropylmethylcellulose, dextrin and hydroxypropylstarch.

12. The cosmetic agent of claim 10, wherein the at least one water-soluble polysaccharide is selected from hydroxypropyl starches.

13. The cosmetic agent of claim 9, wherein the polymer mixture comprises, based on its total weight, at least 80% by weight of:
    a mixture comprising:
       a1) water-soluble vinyl alcohol/vinyl acetate copolymer; and
       a2) at least one water-soluble vinyl alcohol/vinyl acetate copolymers other than the water-soluble vinyl alcohol/vinyl acetate copolymer a1), or
    a mixture, comprising
       a1) water-soluble vinyl alcohol/vinyl acetate copolymer; and
       a2) at least one water-soluble polysaccharide.

14. The cosmetic agent of claim 9, wherein the polymer mixture comprises, based on its total weight, at least 90% by weight of:
    a mixture comprising:
       a1) water-soluble vinyl alcohol/vinyl acetate copolymer; and
       a2) at least one water-soluble vinyl alcohol/vinyl acetate copolymers other than the water-soluble vinyl alcohol/vinyl acetate copolymer a1), or
    a mixture, comprising
       a1) water-soluble vinyl alcohol/vinyl acetate copolymer; and
       a2) at least one water-soluble polysaccharide.

15. The cosmetic agent of claim 9, wherein the polymer mixture comprises, based on its total weight, at least 95% by weight of:
    a mixture comprising:
       a1) water-soluble vinyl alcohol/vinyl acetate copolymer; and
       a2) at least one water-soluble vinyl alcohol/vinyl acetate copolymers other than the water-soluble vinyl alcohol/vinyl acetate copolymer a1), or
    a mixture, comprising
       a1) water-soluble vinyl alcohol/vinyl acetate copolymer; and
       a2) at least one water-soluble polysaccharide.

16. The cosmetic agent of claim 1, wherein the weight ratio of preparation (A) to preparation (B) is from about 10:1 to about 1:10.

17. The cosmetic agent of claim 1, wherein the weight ratio of preparation (A) to preparation (B) is from about 5:1 to about 1:5.

18. The cosmetic agent of claim 1, wherein the weight ratio of preparation (A) to preparation (B) is from about 3:1 to about 1:3.

19. A method for whitening keratin fibers comprising:
preparing a preparation (A) comprising, based on its total weight,
- (a) magnesium carbonate in an amount of from about 5 to about 30% by weight;
- (b) hydrated sodium silicate having a molar ratio $Na_2O:SiO_2$ of from about 1:2 to about 1:3 in an amount of from about 25 to about 50% by weight,
- (c) potassium peroxodisulfate in an amount of from about 20 to about 50% by weight and
- (d) ammonium peroxodisulfate in an amount of from about 1 to about 20% by weight;

preparing a preparation (B) comprising, based on its total weight, at at least one member selected from the group consisting of percarbamide, percarbonates, and perborates in a total quantity of from 0.5 to 95% by weight;

packaging the preparations (A) and (B) separately from one another in a water-soluble film as a cosmetic agent, wherein the preparation (A) and the preparation (B) are each independently in a powder form and/or in a solid form, and wherein the preparation (A) and the preparation (B) are each independently water-free and contain no free hydrogen peroxide;

adding the cosmetic agent to water in order to dissolve the water-soluble film, wherein the volume ratio of the totality of the preparations (A) and (B) to the water is from about 1:1 to about 1:5, to form an application mixture; and treating the keratin fibers with the application mixture.

20. The method of claim 19 wherein the volume ratio of the totality of the preparations (A) and (B) to the water is from about 1:2 to about 1:3.

* * * * *